United States Patent
Bommineni et al.

[11] Patent Number: 6,127,182
[45] Date of Patent: Oct. 3, 2000

[54] RAPID RECOVERY OF SHOOTS THROUGH THIN STEM SLICES AFTER PRECONDITIONING OF MICROPROPAGATED FRUIT TREE SHOOTS

[75] Inventors: Venkata R. Bommineni, Tigard; Helena V. Mathews, Portland, both of Oreg.

[73] Assignee: Agritope, Inc., Portland, Oreg.

[21] Appl. No.: 09/177,758

[22] Filed: Oct. 23, 1998

[51] Int. Cl.$^7$ ............................... C12N 5/04; A01H 5/00
[52] U.S. Cl. .................... 435/430; 435/420; 800/268; 800/315
[58] Field of Search ............................. 435/430, 420; 800/268, 315

[56] References Cited

U.S. PATENT DOCUMENTS 4,361,984  12/1982  Dunstan et al. ........................... 47/58
5,477,000  12/1995  Saxena et al. ........................... 800/200

OTHER PUBLICATIONS

Plant Systematics, Jones, S.B., and A.E. Luchsinger, McGraw–Hill, Inc., p. 354–356, 1986.

Hammerschlag et al, Factors influencing in vitro multiplication and rooting of peach cultivars, Plant Cell Tissue Organ Culture. 8(3). p. 235–242, 1986.

Hammerschlag, F.A., et al. "Factors influencing in vitro multiplication and rooting of peach cultivars," Plant Cell Tissue and Organ Culture, pp. 235–242 (after 1985).

Seifert, G.J., et al., "Rhizogenesis in stem discs of *Malus pumila* rootstock M9 "Jork": I. Hormonal and environmental effects on root induction and callus formation," Plant Cell Reports 14:679–683 (1995).

Viseur, J., "Micropropagation of Pear, Pyrus Coomunis L., In a Double–Phase Culture Medium," Acta Horticulturae 212:117–124 (1987).

Welander.M., "Plant Regeneration from Leaf and Stem Segments of Shoots Raised in vitro from Mature Apple Trees," J. Plant Physiol. 132: 738–744 (1988).

Yepes, L. M., et al, "Micropropagation of thirteen *Malus* cultivars and rootstocks, and effect of antibiotics on proliferation," Plant Growth Regulation 15:55–67 (1994).

Yepes et al., Microproagation of Thirteen Malus Cultivars and Rootstocks, and Effect of Antibiotics on Proliferation, Plant Growth Regulation, 15: 55–67, 1994.

*Primary Examiner*—Gary Benzion
*Assistant Examiner*—Anne Marie Grünberg
*Attorney, Agent, or Firm*—Linda R. Judge

[57] ABSTRACT

An efficient micropropagation system for fruit-bearing trees has been developed for rapid clonal multiplication of large numbers of shoots within a short time. The micropropagation system provides for transformation and vegetative propagation of fruit-bearing tree shoots to produce uniform populations of transgenic fruit-bearing trees.

15 Claims, 2 Drawing Sheets

RAPID RECOVERY OF SHOOTS THROUGH THIN STEM SLICES AFTER PRECONDITIONING OF MICROPROPAGATED FRUIT TREE SHOOTS

Portions of this work were funded by the National Institute of Standards and Technology (NIST) Cooperative Agreement Number 70NANB7H3015.

FIELD OF THE INVENTION

The present invention relates to micropropagation methods for production of large numbers of fruit tree shoots and their rapid clonal multiplication into thousands of shoots within a short period of time. The invention further provides stem-slice methods for the production of transgenic fruit trees, methods for vegetative propagation of transformed shoots and production of mature transgenic fruit trees as well as compositions comprising the same.

BACKGROUND OF THE INVENTION

Apples (Malus species), pears (Pyrus species) and peaches (Prunus species) are important fruit crops in United States with an annual production value of $1.6, 0.3 and 0.4 billion, respectively, from a total of approximately 0.7 million harvested acres (Situation & Outlook Report of USDA-ERS, 1997). Standard techniques for the propagation of fruit trees involve traditional breeding methods such as cuttings or grafting onto root stock which are slow and labor intensive [See, e.g., Viseur, J., *Acta Horticulture* 212:117–124 (1987)].

Considerable effort has been expended to develop methods for large scale reproduction of plants, including fruit-bearing trees. Such methods generally involve tissue culture and micropropagation, providing the advantage of increased rates of clonal propagation of source plants (and therefore yield per time period) (Viseur, J., 1987). Vegetative clonal propagation allows a plant shoot, root or leaf to form a new plant with an exact copy of the genetic information derived from the source tissue maintained in multiple offspring. Accordingly, vegetative propagation provides the advantages of maintenance of superior genotypes and clonal propagation of varieties with particular desirable traits.

It has been demonstrated that fruit tree explants (e.g. nodal segments) can be differentiated into shoots through minor variations in a variety of factors. Some of the factors include, but are not limited to, the source of the explant, the culture medium, the balance of phytohormones (auxins and cytokinins) in the medium, as well as temperature and light [See, e.g., Welander, M., *J. Plant Physiol.* 132:738–744 (1988)].

The success in recovery of plants for a wide variety of species propagated by way of plant tissue culture depends on manipulation of various factors as set forth above. Particularly, the relative quantities of phytohormones in the medium has resulted in standard procedures for micropropagation and recovery of whole plants. Micropropagation procedures involve preparation of explants from the relevant plant, culture of the explant on a medium supplemented with phytohormones, incubation, and recovery of true to type shoots (or shoots with roots) [Douglas, IN: *Methods in Molecular Biology*, Vol. 6, W. Pollard, J. M. Walker, eds. (1990); George and Sherrington, *Exegetics, Ltd.* U.K., p.3 (1984); and Brown and Thorpe, IN: *Cell Culture and Somatic Cell Genetics of Plants*, p49–65, I. K. Vasil, ed. (1986)].

Accordingly, significant research has been directed towards the optimization of physiological conditions of the plant source, selection and culture of explants, and the phytohormones and culture conditions used to initiate formation of shoots.

Current techniques for micropropagation of fruit-bearing trees include nodal culture in which nodal segments from fruit tree twigs are cultured under aseptic conditions in a shoot induction medium [See, Yepes and Aldwinckle, *Plant Growth Regulation*, 15:55–67 (1994), for apple shoots]. Such methods, for example in apple, yield from about 1.3 to 11.6 shoots (depending on germplasm) per explant every 3 to 4 weeks.

Accordingly, there is a need for improved methods for micropropagation of fruit trees, in terms of both the number and clonal nature of fruit tree shoots and corresponding mature fruit trees that may be produced.

In a related area, the potential for cultivar improvement through traditional breeding methods is slow and does not result in production of large numbers of clonal offspring.

The development of gene transfer technology has provided a means for introduction of new traits into proven cultivars without disrupting their otherwise desirable genetic constitutions. (See, e.g., Methods in Plant Molecular Biology and Biotechnology, Glick, B R and Thompson, J E, Eds. CRC Press, 1993).

The work described herein, describes the micropropagation of fruit-bearing trees, based on the invention directed to rapid clonal multiplication of fruit tree shoots. Also disclosed is the recovery of large numbers of native and transgenic fruit trees from such clonal multiplication of fruit tree shoots.

SUMMARY OF THE INVENTION

The present invention represents an improved method for the mass production of clonal plants with the capacity for genetic modification using micropropagation and transformation techniques. Efficient large scale production of economically important temperate fruit crops, e.g., apple, pear, peach and others may be achieved by the vegetative micropropagation methods of the present invention.

The invention is directed to the discovery of an improved method for micropropagation of fruit-bearing trees (or plant species) under conditions that allow for mass production of clonal fruit-bearing trees within a short time period.

In the micropropagation method of the invention, the source of fruit tree shoots can be obtained from nodes of a selected mature fruit tree. After fruit tree explants are established under standard conditions effective to micropropagate the particular species at hand, the explants are preconditioned in an appropriate tissue culture medium in order to produce increased density of leaves and accordingly to increase the source of axillary meristems. The leaves of such preconditioned explants are removed at the petiole region and thin slices made by cross-sectioning the stem explant. The slices are then cultured under conditions effective to yield multiple shoots per explant. The shoots recovered from stem slices may either be further micropropagated by repeating the cycle, or transferred to a medium having the appropriate phytohormones necessary to produce roots and ultimately plandets that are ready to raise under greenhouse and field conditions.

The invention represents a novel method of micropropagation based on the use of stem slices and the discovery of a novel culture medium effective to precondition fruit tree explants resulting in an increase in the density of leaves and a corresponding increase in the source of axillary meristems and the yield of micropropagated fruit tree shoots and fruit tress derived therefrom.

The present invention also provides for the production of transgenic plants using the stem slice method. In the stem slice transformation method of the present invention, target cells (present in the axillary meristems), are readily transformed by introduction of DNA in the form of any of a number of DNA expression vectors or by any of a number DNA delivery methods. Expression vectors effective in the transformation methods of the present invention are exemplified by Agrobacterium-type vectors, plasmid vectors or any other types of vectors containing a gene of interest. The invention further provides expression vectors having tissue or developmental stage specific promoter sequences to target a specific tissues in plants or their products and direct DNA fragment which can be directly introduced into cells of a stem slice explant.

Introduction (delivery) of expression vectors into sliced stem cells can be achieved by various existing methods and includes, but is not limited to, Agrobacterium-mediated transformation, electroporation, microinjection, microprojection by way of particles coated with DNA, laser beams, direct DNA uptake [e.g., by use of polyethylene glycol (PEG), with or without sonication], silicon carbide-mediated or by other methods.

Transformed shoots (mostly chimeric in nature) may then be subjected to various tissue culture manipulations to recover isogenic or pure transgenic shoots or plants. Some exemplary methods for production of transgenic plants are provided in U.S. Pat. No. 5,750,870, incorporated by reference herein, which describes iterative culture methods in strawberry and raspberry, wherein transformed shoots are subjected to repeated cycles of culture and selection, until isolation of a pure transgenic line is achieved. The invention further includes the use of leaves from transformed shoots to generate pure transgenic lines (by regeneration of shoots or plants using various methods of leaf explant manipulation), and other means of tissue culture manipulation or selection which are known to those of skill in the art and may be incorporated into the stem slice method described herein.

These and other objects and features of the invention will be more fully appreciated when the following detailed description of the invention is read in conjunction with the accompanying drawings.

DETAILED DESCRIPTION OF THE INVENTION

I Definitions

Figure 1:
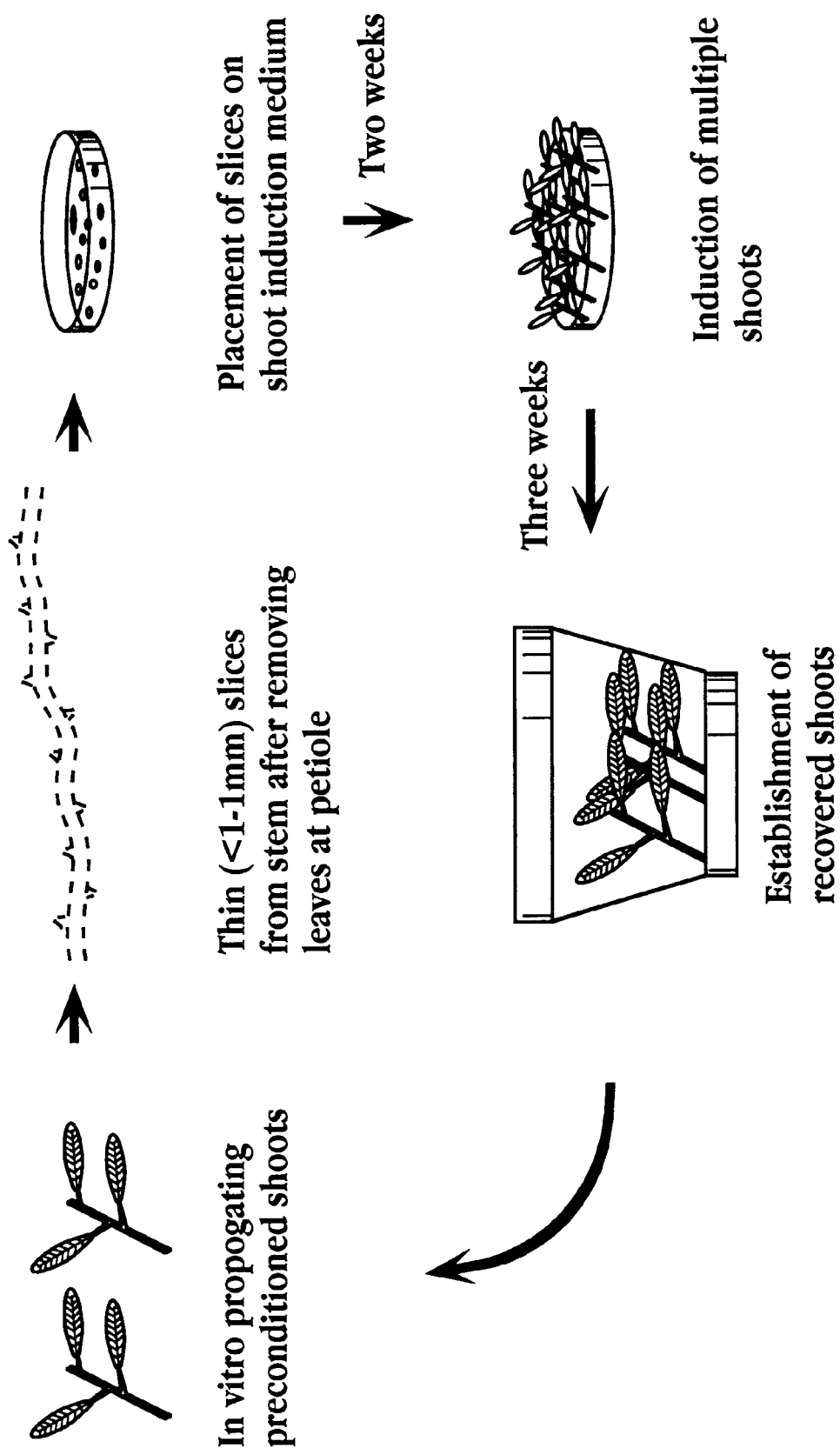
FIG. 1 outlines the stem slice procedure of the present invention.
Figure 2A:
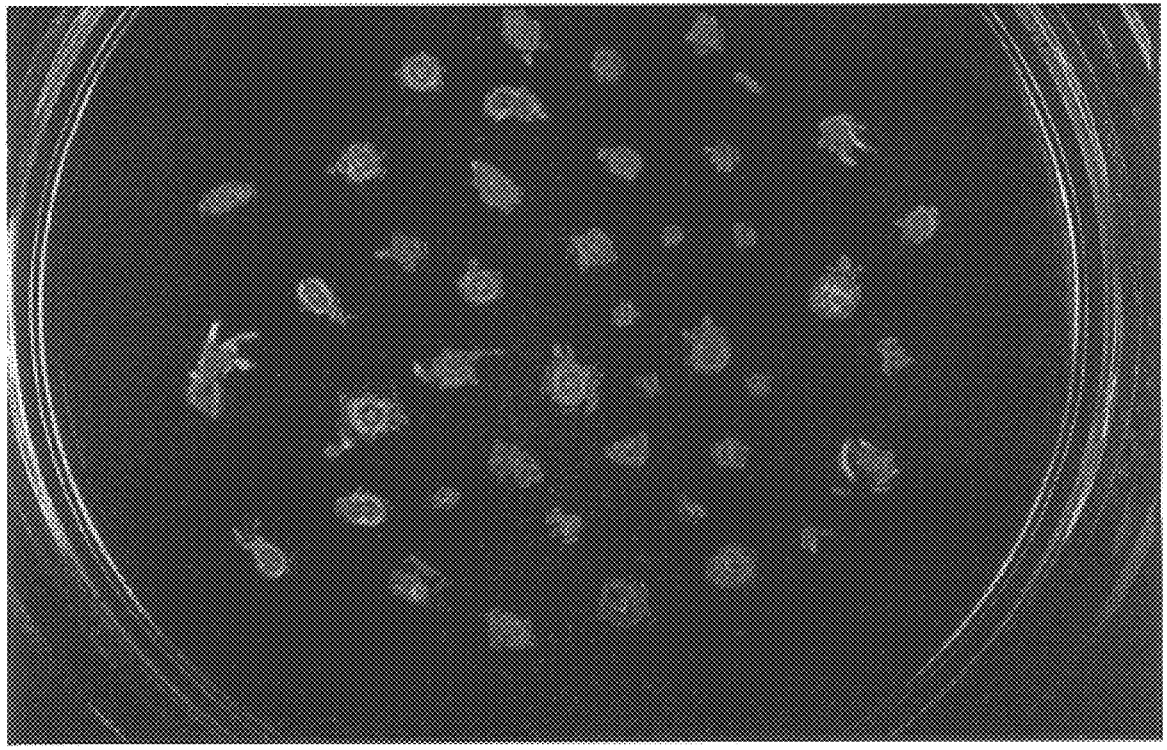
FIG. 2A depicts stem slices at the time of culture following preconditioning and leaf removal for the pear cultivar Bartlett.
Figure 2B:
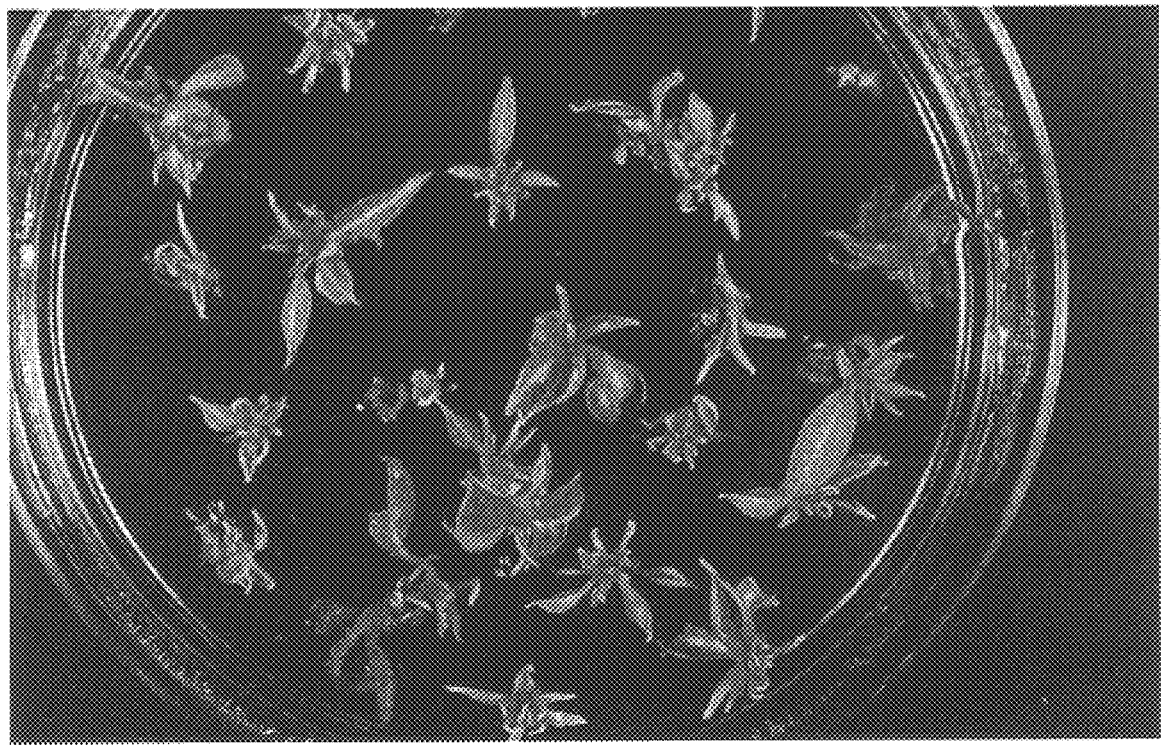
FIG. 2B depicts recovery of shoots from stem slices 32 days after initiation of culture for the pear cultivar Bartlett.

"Apple" as used herein refers to various Malus species. Exemplary varieties or germplasm include Gale Gala, Royal Gala, Red Fuji, Red delicious, and the root stocks of such varieties.

"Pear" as used herein refers to various Pyrus species. Exemplary varieties or germplasm include Bartlett, Anjou, and the root stocks of such varieties.

"Peach" as used herein refers to various Prunus species. Exemplary varieties or germplasm include O'Henry, Red Haven, and the root stocks of such varieties.

The term "germplasm" as used herein refers to the genetic material which forms the physical basis of inherited qualities and is transmitted from generation to generation by the germ cells [from Reiger et al., GLOSSARY OF GENETICS, CLASSICAL AND MOLECULAR, Springer-Verlag, (1991)].

The term "explant" as used herein refers to the thin stem slices (with cross-sectioned axillary meristems), which upon culture in the appropriate medium can develop into shoots or plantlets.

The term "axillary meristem" as used herein refers to the plant tissue at the junction of the leaves and the shoots, which is capable of developing into an entire plant when cultured under appropriate conditions.

As used herein the term "conditions effective to increase leaf density" refers to plant tissue culture conditions and tissue culture medium containing a combination of phytohormones and nutrients in the relative amounts recited below effective to result in an increase the density of leaves and accordingly the density of axillary meristems of fruit tree explants cultured therein. As will be appreciated, such "conditions effective to increase leaf density" will vary depending upon the type of fruit tree explant to which they are applied.

As used herein "conditions effective to increase shoot density" refers to the standard plant tissue culture conditions known to those of skill in the art to increase the density of shoots. Although such conditions are "standard", as will be appreciated, such conditions will vary depending upon the type of fruit tree or plant explant to which they are applied.

As used herein "micropropagation" refers to in vitro asexual clonal reproduction of plants wherein large numbers of new shoots may be obtained in a short time period from the cells, tissues, or organs of parental plants by culture in a medium containing plant hormones, minerals, vitamins and carbohydrates in the appropriate concentrations.

"Transformed", "stably transformed" or "transgenic" as used herein refers to a cell derived from a fruit tree or a plant that has foreign nucleic acid integrated into its genome which is maintained from one generation to another.

"Cell culture" as used herein refers to a culture of plant cells, typically explants or stem slices derived therefrom, cultured in a suitable growth medium.

II. Micropropagation Method

The fruit tree micropropagation method of the present invention, initial (primary) explants (nodal) are preferably derived from the twigs of mature fruit trees (proprietary germplasm from Van Well Nurseries, Wenatchee, Wash.). Exemplary fruit-bearing trees are apple, pear and peach. Alternatively, fruit tree explants may be prepared from immature flower buds, zygotic embryos or other grafting methods.

Micropropagation allows for the production of large numbers of plants in a relatively short period of time. Once established, actively dividing cultures are a continuous source of tissue for further propagation, which can result in vegetative production of clonal plants that maintain superior traits of original source plants. Depending on the species, the original source tissue is taken from sources such as shoot tip, leaf, lateral bud, nodal segment, stem (twig) with some younger nodes, or root tissue. The explant is surface sterilized and used to establish a culture of the tissue under aseptic conditions in the appropriate culture medium that allows proliferation of buds and adventitious shoots. Subculture of buds or shoots is repeated until multiple shoots are produced, all having the genetic characteristics of the original source tissue. The average rate of propagation depends on the plant species. In general, shoots are separated on an average of every four weeks and transferred to fresh proliferation medium to repeat the same process in a cyclical manner. The micropropagated shoots are later transferred to root inducing medium to recover plantlets [See, e.g., Seifert et al., *Plant Cell Reports* 14:679–683 (1995)].

In the micropropagation method of the invention, preferably, the original explants come from mature fruit tree twigs that are cut into small pieces (approximately 6 to 8 cm long twigs comprising more than 3 nodes), surface sterilized by standard tissue culture methods and placed in a standard micropropagation medium.

Following culture in standard micropropagation medium, nodes with axillary meristems are excised and placed onto initial medium to establish in vitro culture of shoots. Shoots are formed within 3 to 6 weeks, transferred to fresh propagation medium until they are established under in vitro conditions, then transferred to preconditioning medium to maximize the density of leaves.

In the method of the invention, the leaves of the preconditioned explants are removed and thin slices of the explants prepared and cultured under conditions effective to yield a maximum number of shoots.

In a preferred embodiment, stem slices are prepared from preconditioned micropropagated shoots of fruit trees.

In order to facilitate production of a large number of leaves, primary explants are preconditioned in tissue culture medium which contains one or more plant growth regulators, a cytokinin, exemplified by 6-benzyl amino purine and kinetin, and an antibiotic, e.g., cefotaxime.

This preconditioning procedure results in an increase in the number of leaves, each leaf containing an axillary meristem as a source for multiplication of shoots. Random slices (thin cross sections) are made after removing the leaves. A 1 cm shoot may have 10–20 axillary meristems (i.e. leaves) and thin (1 mm) slices are made through leaf initial regions (i.e. nodal regions) throughout the stem. Preferably, more than 2 slices are made through the axillary meristem regions (i.e. leaf initial regions) to recover one or more shoots per slice.

The number of shoots produced per stem slice is preferably 2, more preferably 3, and most preferably 4 or more. Optimal shoot production within a short time period is preferred to increase the yield of plantlets, as well as for use in the plant transformation methods described herein.

Preferably, stem slices are from about 0.8 to 1 mm thick. In general, slices of this thickness retain sufficient cells for recovery of meristems and are able to develop into shoots.

Using the methods described herein, multiple shoots were recovered from most slices. In general, every slice produced by the methods described herein has sufficient meristem cells to recover and produce shoots. [See e.g., a discussion of meristem reorganization in maize by Bommineni et al, *Maydica* 40: 289–298 (1995)]. The recovered shoots may either be further multiplied by repeating the cycle or transferred to a medium having the appropriate phytohormones under conditions necessary to produce shoots with roots (i.e., plantlets) followed by planting in soil to obtain mature fruit-bearing trees.

Current techniques for micropropagation of fruit-bearing trees include nodal culture in which nodal segments from fruit tree twigs are cultured under aseptic conditions in a shoot induction medium [See, Yepes and Aldwinckle, *Plant Growth Regulation*, 15:55–67 (1994), for apple shoots]. Such methods, for example in apple, yield from about 1.3 to 11.6 shoots (depending on germplasm) per explant every 3 to 4 weeks.

The micropropagation method of the present invention yields an average of 2 shoots per stem slice with approximately 20 to 25 slices obtained from a single explant that is about 1 to 1.5 cm long. This represents cross-sectional slices of less than or equal to 1 mm along the length of each shoot.

Accordingly, the present invention represents a 5 to 40 fold increase in the yield of shoots which may be generated, relative to current techniques for micropropagation of fruit tree shoots. This increase in the yield of fruit tree shoots is ultimately reflected in an increased yield of regenerated clonal fruit trees.

The stem slices of the present invention also provide an opportunity for improvement of fruit-bearing trees by introduction of new genetic traits into the stem slices through the various transformation techniques described above which are effective to result in stable transformation of cells within the stem slices. The transformation methods which are known to those of skill in the art and have been proven in different plant species and involve the introduction of selected genes into existing germplasm without disrupting the otherwise desirable genetic make-up. In addition, the stem slice method described herein provides a faster means to vegetatively propagate large number of either non-transformed or transformed clonal fruit trees.

The present invention includes a novel method for the micropropagation of fruit-bearing trees based on a stem slice technique which allows for mass propagation and introduction of selected genes of interest into cells within slices of fruit tree stems and recovery of genetically engineered fruit-bearing trees. The trees are vegetatively propagated allowing for preservation of transgenes and their selective expression in target tissues.

The present invention includes the direct and indirect application of the stem slice procedure in transformation of fruit-bearing plants and compositions produced by the methods described herein.

The following example illustrates but is not intended in any way to limit the invention.

EXAMPLE 1

Preparation and Micropropagation of Fruit Tree Explants

Leaves were excised from the twigs of mature pear (var. Bartlett) and apple (var. Gale Gala) fruit trees. The twigs were cut into small pieces approximately 6 to 8 cm in length, and surface sterilized by standard tissue culture procedures. Generally, two to three nodal segments from each twig were excised and placed on initial culture medium. These nodal segments typically contain the axillary meristems or buds.

The initial medium for establishment of pear (var. Bartlett) and apple (var. Gale Gala) in vitro culture consists of phytagel solidified basal medium with salts of Quoirin and Lepoivre [*Acta Hortic* 78:437–442 (1977)], Murashige and Skoog salts [Physiol. Plant 15: 473–497 (1962)], salts of Lloyd and McCown [Woody plant medium, *Int. Plant Prop. Soc. Proc.* 30: 421–427 (1981)] or Nitsch and Nitsch salts [N6 salts, *Amer. J. Bot.* 43: 839–851 (1956)] and supplemented with Staba or B5 vitamins, and varying concentrations of glycine, sucrose, antibiotics, plant preservation mixture (PPM), auxins and cytokinins.

Shoot formation was observed in 4 to 6 weeks after incubation in initial medium. Contamination-free shoots were then transferred to routine MICROPROPAGATION medium. Pear (var. Bartlett) MICROPROPAGATION medium consists of phytagel (0.25%) solidified Quoirin and Lepoivre, Staba vitamins, glycine (2 mg/L), sucrose (30 g/L), cefotaxime (300 mg/L), 6-benzyl amino purine (3 mg/L), and kinetin (5 mg/L). For apple (var. Gale Gala), MICROPROPAGATION medium consists of phytagel solidified (0.25%) medium with salts of Murashige and Skoog, B5 vitamins, glycine (2 mg/L), sucrose (30 g/L), Cefotaxime (200 mg/L), 6-benzyl amino purine (1 or 2 mg/L) and kinetin (3 or 5 mg/L). The routine MICROPROPAGATION medium was also used for preconditioning the shoots for stem slice culture and recovery of multiple shoots from stem slices. The ingredients of routine MICROPROPAGATION medium may be modified from time to time depending on regular transfers (e.g., to promote elongation of shoots, major salts in the medium were replaced with major salts from a different medium). The composition of preconditioning medium remains the same as described above with 6 to 8 weeks of preconditioning time required to achieve high leaf density and maximum yield of multiple shoots. Optimization of cytokinin and auxin ratios, the level of cefotaxime (or an equivalent antibiotic) and other components of the medium may be required for different cultivars or plant species. Using the methods described herein, such optimization may be easily accomplished by one of skill in the art.

The following table summarizes the percent of stem slices with recovered shoots and the mean number of shoots obtained per stem in pear (cv. Bartlett) and apple (cv. Gale Gala).

TABLE 1

| Fruit Tree | Treatment* [number (n) and length of stem] | Total # of slices | # of slices with shoots (%) | Mean # of shoots per stem ± S.D. (responding slices) | Maximum # of shoots obtained from a given stem (length) |
|---|---|---|---|---|---|
| Pear (cv Bartlett) | BAR3-3 and BAR3-3d (n = 8; 1–1.5 cm) | 319 | 300 (94%) | 75 ± 30 | 126 (1.5 cm) |
| Pear (cv Bartlett) | BAR3-4 and BAR3-4d (n = 5; 1–1.5 cm) | 143 | 88 (61%) | 51 + 24 | 79 (1.5 cm) |
| Apple (cv Gale Gala) | GGR5-1 and GGR5-ld (n = 10; 1–2 cm) | 476 | 116 (25%) | 18 ± 18 | 56 (1.5 cm) |
| Apple (cv Gale Gala) | GGR5-2 and GGR5-2d (n = 11; 1–1.5 cm) | 405 | 90 (22%) | 13 ± 8 | 24 (1 cm) |

*BAR = Bartlett regeneration medium; GGR = Gale Gala regeneration medium; d = kept in dark for two weeks and transferred to light conditions Following recovery of shoots, leaves were removed from the shoots and multiple cross-sectional slices of less than or equal to 1 mm were made along the length of each shoot, followed by placing the slices on shoot recovery medium for about 2–4 weeks. The shoot recovery medium comprises the same components as the routine MICROPROPAGATION medium for pear (var. Bartlett) and apple (var. Gale Gala), respectively. In addition, phytagel (0.25%) solidified medium with salts of Woody Plant medium (WPM), B5 vitamins, glycine (2 mg/L), sucrose (30 g/L), cefotaxime (200 mg/L), 6-benzyl amino purine (1 mg/L) and kinetin (3 mg/L) are used for apple (var. Gale Gala).

The shoots recovered from stem slices may either be further micropropagated by repeating the cycle, or transferred to a medium having the appropriate phytohormones necessary to produce roots and ultimately plantlets that are ready to raise under greenhouse and field conditions, as described above.

While the invention has been described with reference to specific methods and embodiments, it will be appreciated that various modifications and changes may be made without departing from the invention. All patent and literature references cited herein are hereby incorporated by reference in their entireties.

It is claimed:

1. A method for micropropagating rosaceous trees comprising
   (i) preparing explants from twigs of rosaceous tree stems under aseptic conditions;
   (ii) culturing said explants in a suitable culture medium under conditions effective to generate shoots;
   (iii) preconditioning said shoots in a suitable culture medium under conditions effective to increase the density of leaves and axillary meristems;
   (iv) removing leaves from said preconditioned shoots;
   (v) making thin slices of said preconditioned shoots wherein said thin slices consist of at least part of an axillary meristem of said shoot; and
   (vi) culturing said thin slices under conditions effective to generate multiple shoots.

2. The method of claim 1, wherein said rosaceous tree is selected from the group consisting of apple trees (Malus species), pear trees (Pyrus species), peach trees (Prunus species), and any other rosaceous tree species.

3. The method of claim 1, wherein said preconditioning culture medium comprises cytokinins and cefotaxime.

4. The method of claim 1, wherein said stem slices correspond to a thickness of 1 mm or less.

5. The method of claim 1 or 4 for micropropaating and recovering viable rosaceous trees, further comprising the steps of
   (vii) culturing said multiple shoots under conditions effective to generate roots;
   (viii) further culturing said shoots to produce plantlets; and (ix) treating said plantlets in a manner effective to generate plants.

6. A fruit tree and other plant shoot having an increase in the number of axillary meristems and leaves compared to a fruit tree shoot prepared under standard micropropagation techniques, the improvement comprising at least a 10 fold increase in the number of leaves and axillary meristems by exposing said fruit tree shoot to tissue culture conditions effective to produce said increase.

7. A method for producing transgenic fruit-bearing trees comprising
   (i) introducing a DNA expression vector comprising a gene of interest and a selectable marker, into a target explant having meristem cells under conditions effective to stably incorporate said gene of interest into said meristem cells;
   (ii) culturing transformed shoots in tissue culture medium containing a selective agent wherein transformed plant cells expressing said selectable marker are selectively propagated;
   (ii) culturing said explants under shoot recovery conditions to produce transgenic shoots;
   (iii) generating explants from the recovered transgenic shoots;
   (iv) repeating steps (ii) through (iv), wherein said transformed explants are cultured in tissue culture medium having a higher concentration of selective agent in each successive cycle; until pure transgenic explants are obtained; and
   (v) producing transgenic plants by recovering plants from the pure transgenic explants.

8. A method of claim 7, where said pure transgenic explants are identified by dividing the recovered shoots into explants, culturing the explants, and verifying that the growth of all explants is resistant to the highest concentration of selective agent used.

9. A method of claim 7, where said fruit tree is selected from the group consisting of apple trees, pear trees, peach trees and other rosaceous plant species.

10. The method of claim 1 further comprising:
    repeating steps (iii) to (vi) one or more times.

11. A method for micropropagating apple, pear and peach trees, comprising:
    (i) preparing explants from twigs of apple, pear or peach tree stems under aseptic conditions;
    (ii) culturing said explants in a suitable culture medium under conditions effective to generate shoots;
    (iii) preconditioning said shoots in a suitable culture medium under conditions effective to increase the density of leaves and axillary meristems;
    (iv) removing leaves from said preconditioned shoots;
    (v) making thin slices of said preconditioned shoots wherein said thin slices consist of all or part of an axillary meristem of said shoot; and
    (vi) culturing said thin slices under conditions effective to generate multiple shoots.

12. The method of claim 11, wherein said preconditioning culture medium comprises cytokinins and cefotaxime.

13. The method of claim 11, wherein said stem slices correspond to a thickness of 1 mm or less.

14. The method of claim 11, further comprising:
    repeating steps (iii) to (vi) one or more times.

15. The method of claim 11 or 14 further comprising the steps of:
    (vii) culturing said multiple shoots under conditions effective to generate roots;
    (viii) further culturing said shoots to produce plantlets; and
    (ix) treating said plantlets in a manner effective to generate plants.

* * * * *